US008114121B2

(12) United States Patent
Viola

(10) Patent No.: US 8,114,121 B2
(45) Date of Patent: Feb. 14, 2012

(54) TISSUE VITALITY COMPARATOR WITH LIGHT PIPE WITH FIBER OPTIC IMAGING BUNDLE

(75) Inventor: Frank J. Viola, Sandy Hook, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 1305 days.

(21) Appl. No.: 11/473,296

(22) Filed: Jun. 22, 2006

(65) Prior Publication Data

US 2007/0299468 A1 Dec. 27, 2007

(51) Int. Cl.
*A61B 17/00* (2006.01)

(52) U.S. Cl. .......................................... 606/206; 606/16

(58) Field of Classification Search .................. 600/117, 600/127, 342, 367, 477–478, 564–566; 606/49, 606/205–209, 16
See application file for complete search history.

(56) References Cited

U.S. PATENT DOCUMENTS

| 5,336,232 | A | | 8/1994 | Green et al. | |
|---|---|---|---|---|---|
| 5,569,300 | A | * | 10/1996 | Redmon | 606/207 |
| 5,667,473 | A | * | 9/1997 | Finn et al. | 600/104 |
| 5,674,230 | A | * | 10/1997 | Tovey et al. | 606/139 |
| 5,762,613 | A | * | 6/1998 | Sutton et al. | 600/564 |
| 5,772,597 | A | * | 6/1998 | Goldberger et al. | 600/473 |
| 5,785,658 | A | * | 7/1998 | Benaron et al. | 600/473 |
| 5,800,350 | A | * | 9/1998 | Coppleson et al. | 600/372 |
| 5,879,289 | A | * | 3/1999 | Yarush et al. | 600/179 |
| 5,941,822 | A | * | 8/1999 | Skladnev et al. | 600/407 |
| 6,010,516 | A | * | 1/2000 | Hulka | 606/148 |
| 6,129,683 | A | * | 10/2000 | Sutton et al. | 600/564 |
| 6,226,543 | B1 | | 5/2001 | Gilboa et al. | |
| 6,324,418 | B1 | * | 11/2001 | Crowley et al. | 600/476 |
| 6,419,626 | B1 | * | 7/2002 | Yoon | 600/109 |
| 6,558,333 | B2 | | 5/2003 | Gilboa et al. | |
| 6,711,429 | B1 | | 3/2004 | Gilboa et al. | |
| 6,796,939 | B1 | * | 9/2004 | Hirata et al. | 600/179 |
| 6,882,875 | B1 | * | 4/2005 | Crowley | 600/407 |
| 7,306,559 | B2 | * | 12/2007 | Williams | 600/245 |
| 7,310,547 | B2 | * | 12/2007 | Zelenchuk | 600/407 |
| 7,615,002 | B2 | * | 11/2009 | Rothweiler et al. | 600/104 |
| 2004/0054270 | A1 | | 3/2004 | Pewzner et al. | |
| 2005/0033556 | A1 | | 2/2005 | Miura | |
| 2005/0203562 | A1 | | 9/2005 | Palmer et al. | |
| 2006/0161055 | A1 | * | 7/2006 | Pewzner et al. | 600/310 |
| 2006/0235279 | A1 | | 10/2006 | Hawkes et al. | |
| 2007/0078484 | A1 | * | 4/2007 | Talarico et al. | 606/205 |

FOREIGN PATENT DOCUMENTS

WO    WO 97/41776    11/1997

OTHER PUBLICATIONS

European Search Report for EP 07252541.3-1265 date of completion is Sep. 24, 2007 (7 pages).

* cited by examiner

*Primary Examiner* — Kevin C Sirmons
*Assistant Examiner* — Brandy C Scott

(57) ABSTRACT

A surgical instrument having a tissue vitality comparator is provided to view images of tissue relative to the surgical instrument and compare the images with predetermined reference images. The surgical instrument includes a pair of jaws for capturing tissue and one or more light sources 14 illuminating the captured tissue. The surgical instrument additionally includes a light pipe with fiber optic imaging bundle having a first end for viewing the tissue between the jaws and a second end on a handle portion of the surgical instrument for observing the tissue. A tissue comparison chart having a plurality of reference images is provided on the handle of the surgical instrument for comparison with the image observed through the second end of the light pipe with fiber optic imaging bundle.

9 Claims, 4 Drawing Sheets

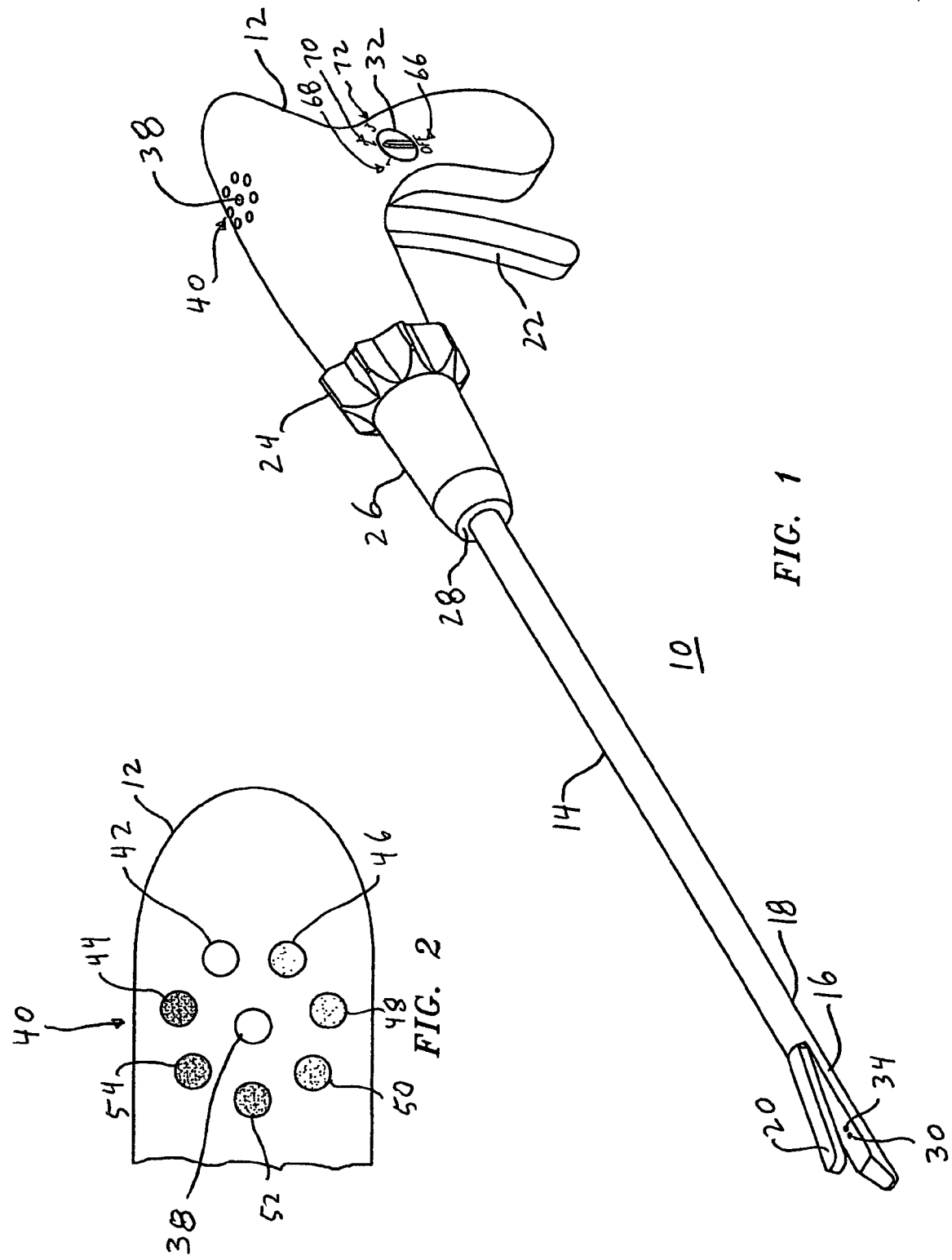

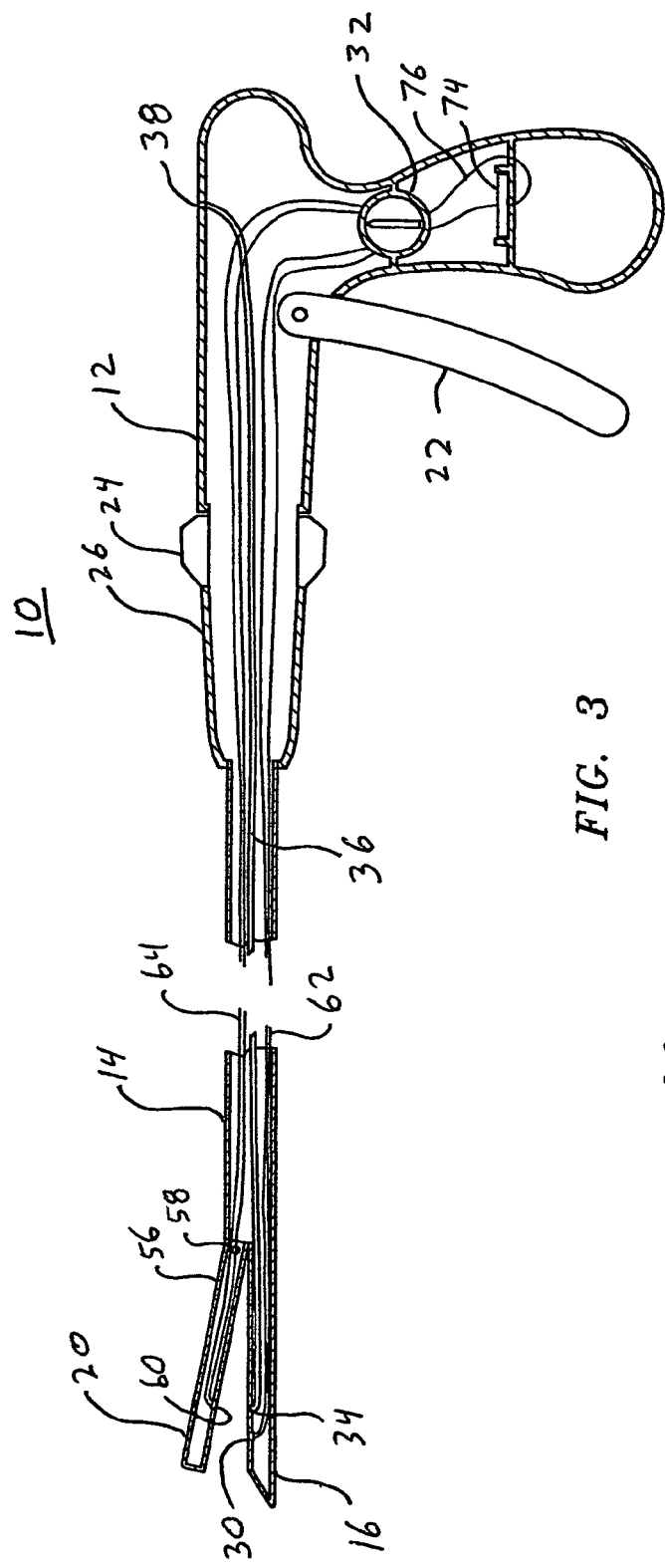
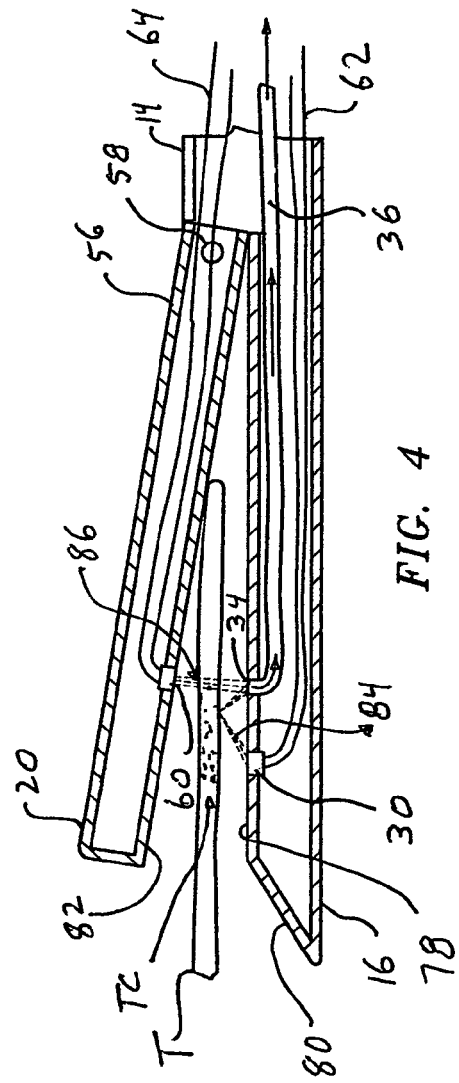
FIG. 3
FIG. 4

TISSUE VITALITY COMPARATOR WITH LIGHT PIPE WITH FIBER OPTIC IMAGING BUNDLE

BACKGROUND

1. Technical Field

The present disclosure relates to surgical instruments having a comparator for evaluating tissue vitality during surgery. More particularly, the present disclosure relates to surgical instruments incorporating a tissue vitality comparator having a light pipe with fiber optic imaging bundle to convey an image of a specific area of tissue, contained within the jaws of the surgical instrument, to a surgeon.

2. Background of Related Art

Various surgical instruments are known in the art which are useful in performing operations on specific areas of tissue. Typically, the areas of tissue operated on are diseased or otherwise in need of surgical intervention.

Most such surgical instruments are designed to capture tissue between one or more jaws associated with the surgical instruments. Operations typically performed with these surgical instruments may include grasping, cutting, stapling, obtaining tissue measurements, etc. One type of surgical instrument incorporates jaw structure which move in pivotal fashion relative to each other in order to grasp and operate on tissue captured therebetween.

Alternative types of surgical instruments have jaw structure which move parallel to each other to grasp and manipulate tissue. Such instruments may include general gastrointestinal staplers, end to end anastomosis devices used to connect tubular tissue sections, etc. Additionally, instruments such as tissue measuring devices disclosed in U.S. Pat. No. 5,336,232 to Green et al. incorporate parallel jaw movement to obtain accurate measurements of tissue thickness.

During operation of these various surgical instruments it is often necessary to position the jaw structure relative to specific areas of tissue. This is typically accomplished by direct visual observation of the tissue in question. Often however, the tissue is obscured or other wise inhibited from view. Furthermore, in some instances, when direct observation of tissue is used to position the surgical instrument relative to tissue, the positioning of the surgical instrument is difficult to position accurately. It is also desirable to determine the condition of tissue prior to operation of a surgical instrument on the tissue.

Thus, there exists a need for a surgical instrument having an optical system for accurately positioning jaws associated with the surgical instrument relative to the tissue section desired to be operated upon. Furthermore, there exists a need for a surgical instrument having a reference chart or graph for comparing the images observed through the optical system with known reference images to more accurately position the surgical instrument relative to the tissue.

SUMMARY

There is disclosed a surgical instrument for manipulating and viewing tissue during surgery. The surgical instrument generally includes a housing having at least one jaw extending from the housing and a light source positioned on the at least one jaw. A light pipe with fiber optic imaging bundle extends between the at least one jaw and the housing. The light pipe with fiber optic imaging bundle has a first end positioned on the at least one jaw and the second end positioned on the housing such that an image illuminated by the light source is visible at the housing. The housing has an elongate member extending distally from the housing and a first jaw and a second jaw mounted on the distal end of the elongate member. The first jaw and the second jaw are movable with respect to one another. In one embodiment, the first and second jaws are mounted for pivotal movement relative to each other. In an alternative embodiment, the first and second jaws are mounted for parallel movement relative to each other.

The first end of the light pipe with fiber optic imaging bundle is positioned on the first jaw. In one embodiment, the light source is positioned on the first jaw, while in an alternative embodiment, the light source is positioned on the second jaw.

In a specific embodiment, the light source is an LED light source and the housing includes a power source for the LED light source and a switch to activate the LED light source. Other light sources may be used.

In a particular embodiment, the housing includes a tissue comparison chart positioned on the housing adjacent the second end of the light pipe with fiber optic imaging bundle. The tissue comparison chart at least partially surrounds the second end of the light pipe with fiber optic imaging bundle. In one embodiment, the tissue comparison chart includes a first reference image corresponding to healthy tissue and a second reference image corresponding to unhealthy tissue. Intermediate references may include various levels of tissue degradation, for comparison.

There is also disclosed the surgical instrument having a housing, an elongate member extending distally from the housing and a first jaw and a second jaw mounted for relative movement on the distal end of the elongate member. The surgical instrument includes a light pipe with fiber optic imaging bundle having a first end positioned on the first jaw and a second end positioned on the housing. At least one light source is positioned on one of the first and second jaws. The housing includes a power source for the light source and a tissue comparison chart positioned on the housing. In one embodiment, the at least one light source is positioned on the first jaw adjacent the first end of the light pipe with fiber optic imaging bundle. In an alternative embodiment, the at least one light source is positioned on the second jaw opposite the first end of the light pipe with fiber optic imaging bundle.

There is also disclosed a method of visualizing tissue using a surgical instrument which includes providing a surgical instrument having a housing, and the elongate member extending distally from the housing and a first jaw and a second jaw mounted for relative movement on the distal end of the elongate member. The surgical instrument additionally includes a light pipe with fiber optic imaging bundle having a first end positioned on the first jaw and a second end positioned in the housing and at least one light source positioned on at least one of the first and second jaws. A power source for the light source and a tissue comparison chart are positioned on the housing.

The method includes the step of illuminating tissue positioned between the first and second jaws with the at least one light source and viewing the illuminated tissue through the second end of the light pipe with fiber optic imaging bundle. In one embodiment, the tissue is illuminated with a light source positioned on the first jaw such that the tissue is viewed with the light reflecting off the tissue. In an alternative embodiment, the tissue is illuminated with a light source positioned on the second jaw such that the tissue is viewed with the light transmitted through the tissue.

The method further includes the step of comparing the illuminated tissue with the tissue comparison chart.

DESCRIPTION OF THE DRAWINGS

Various embodiments of the presently disclosed surgical instrument having a tissue vitality comparator are disclosed herein with reference to the drawings, wherein:

FIG. 1 is a perspective view of one embodiment of the presently disclosed surgical instrument with tissue vitality comparator having pivoting jaw structure;

FIG. 2 is a top view of a portion of a handle of the surgical instrument illustrating a viewing window and comparison chart;

FIG. 3 is a side view, shown in section, of the surgical instrument of FIG. 1;

FIG. 4 is an enlarged side view, shown in section, of the distal end of the surgical instrument of FIG. 1;

DETAILED DESCRIPTION OF EMBODIMENTS

Figure 5:
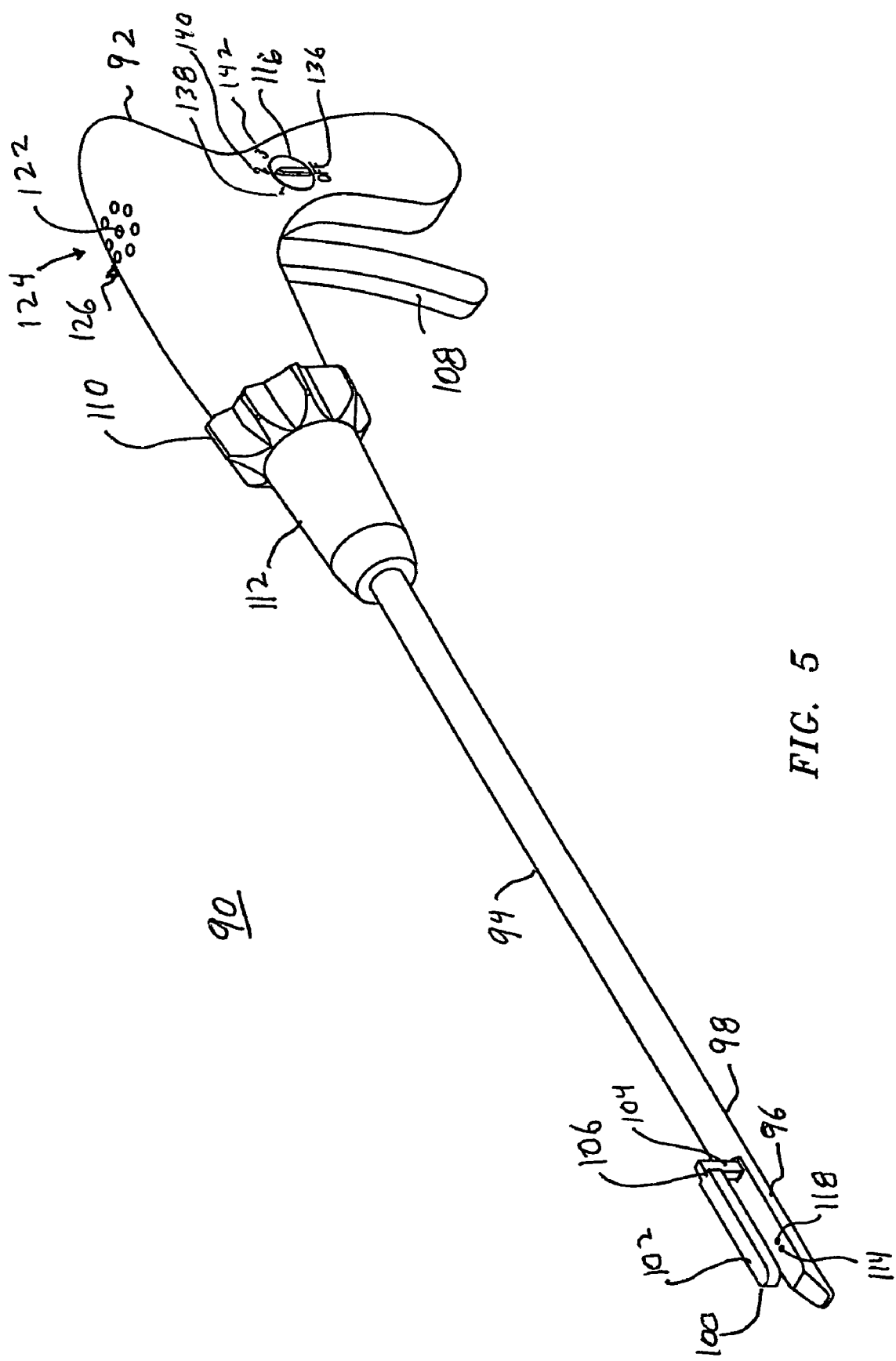
FIG. 5 is a perspective view of another embodiment of a surgical instrument with a tissue vitality comparator having a parallel closure jaw structure.

Embodiments of the presently disclosed surgical instrument having a tissue vitality comparator will now be described in detail with reference to the drawings wherein like numerals designate identical or corresponding elements in each of the several views. As is common in the art, the term "proximal" refers to that part or component of the surgical instrument closer to the user or operator, i.e. surgeon or physician, while the term "distal" refers to that part or component of the surgical instrument further away from the user.

Referring to FIG. 1, there is disclosed a surgical instrument having a tissue vitality comparator (hereinafter "TVC") or surgical instrument 10 suitable for use in performing operations on tissue while at the same time capable of allowing the surgeon to optically view the tissue being operated on. Specifically, surgical instrument 10 allows the surgeon to view the tissue being operated on and, at the same time, compare the image of the tissue to predetermined reference images. The predetermined reference images may include those related to the color, texture, or other characteristics of animal tissue.

Surgical instrument 10 generally includes a housing that forms a handle 12 having an elongate member 14 extending distally from handle 12. A first jaw 16 is mounted on a distal end 18 of elongate member 14. As shown, in this particular embodiment, first jaw 16 is stationary relative to elongate member 14 and maybe integrally formed therewith. A second jaw 20 is also mounted on distal end 18 of elongate member 14. Second jaw 20 is movable relative to first jaw 16 and elongate member 14. An actuator 22 is provided on handle 12 to move second jaw 20 between an open position spaced apart from first jaw 16 to a closed position adjacent first jaw 16.

Surgical instrument 10 can be based on various surgical instruments having pivoting jaw structure typically used for grasping, cutting, stapling, etc. or otherwise manipulating tissue. In this embodiment, second jaw 20 is mounted for pivotal movement relative to first jaw 16 and elongate member 14 such that second jaw 20 moves through an arc relative to first jaw 16.

Surgical instrument 10 includes an actuator 22 for use in moving second jaw 20 between the open and closed positions and a rotator 24 which is configured to rotate a nose cone portion 26 of handle 12. Elongate member 14 extends from a distal end 28 of nose cone portion 26 such that rotation of rotator 24 serves to rotate first and second jaws 16 and 20 and orient them relative to the tissue being operated upon.

As noted hereinabove, surgical instrument 10 includes a TVC for use in optically observing the tissue being operated upon and comparing that viewed image with reference images. Surgical instrument 10 includes a first light source 30 positioned on first jaw 16 to illuminate tissue positioned between first jaw 16 and second jaw 20. Surgical instrument 10 additionally includes a multi-position switch 32 for operating first light source 30 as well as additional light sources described in more detail hereinbelow.

In order to view the tissue captured between first jaw 16 and second jaw 20, surgical instrument 10 is provided with a first end 34 of a light pipe with fiber optic imaging bundle 36 (FIG. 3) positioned on first jaw 16. A second end 38 of light pipe with fiber optic imaging bundle 36 is positioned on handle 12 to allow the surgeon or operator to optically view tissue captured between first jaw 16 and second jaw 20.

Referring now to FIGS. 1 and 2, surgical instrument 10 is provided with a tissue comparison chart 40 positioned on handle 12. Tissue comparison chart 40 is positioned adjacent second end 38 of light pipe with fiber optic imaging bundle 36 so as to compare the image viewed through light pipe with fiber optic imaging bundle 36 with images associated with tissue comparison chart 40. Tissue comparison chart 40 is provided with a plurality of reference images which may correspond to color, texture, or other characteristics of tissue so that surgical instrument 10 may be properly positioned relative to the exact or specific area of tissue desired to be operated upon.

Tissue comparison chart 40 includes a first reference image 42 which generally corresponds to healthy tissue. At an opposite end of the spectrum, tissue comparison chart 40 includes a second reference image 44 which corresponds to unhealthy tissue. A plurality of intermediate reference images 46, 48, 50, 52 and 54 are provided on tissue comparison chart 40 to allow the surgeon or operator to evaluate the condition of the tissue. Depending upon the particular use of surgical instrument 10, an intermediate reference image, such as reference image 50, may correspond to that associated with the limit of potentially viable tissue.

Referring now to FIG. 3, as noted hereinabove second jaw 20 is mounted for pivotal movement relative to first jaw 16. A proximal end 56 of second jaw 20 is attached to elongate member 14 at pivot point 58 such that second jaw 20 may move through an arc relative to first jaw 16 in response to motion of actuator 22.

Second jaw 20 is provided with a second light source 60 positioned generally opposite first end 34 of light pipe with fiber optic imaging bundle 36. This allows second light source 60 to transmit light through tissue generally positioned between first jaw 16 and second jaw 20 such that the image of tissue observed by light pipe with fiber optic imaging bundle 36 is by way of light transmitted through the tissue. In a particular application, light pipe with fiber optic imaging bundle 36 is a conventional fiber optic connecting first end 34 of light pipe with fiber optic imaging bundle 36 to second and 38 of light pipe with fiber optic imaging bundle 36 to thereby transmit an image therethrough. Alternatively, light pipe with fiber optic imaging bundle 36 may be configured of other alternative means of transmitting an image from first end 34 to second end 38 of light pipe with fiber optic imaging bundle 36. For example, electrical means of transmitting digitized images may be utilized, etc.

As shown, a first pair of wires 62 extend through first jaw 16, elongate member 14 and handle 12 to connect first light source 30 with multi-position switch 32 positioned in handle 12. Similarly, a second pair of wires 64 connects second light source 62 with multi-position switch 32.

It should be noted that first and second light sources 30 and 60 may be LED type light sources. In particular applications, the use of LED type light sources may be particularly desirable as they generate little heat and have little or no impact upon the characteristics of the tissue being observed. This may assist in ensuring that surgical instrument 10 does not obtain a false image of the tissue being observed. In alternative applications, first and second light sources 30 and 60 may be conventional incandescent, infrared or other type light sources.

As shown in FIG. 1, multi-position switch 32 is provided with several positions to control first and second light sources 34 and 60, respectively. Multi-position switch 32 is provided with a first position 66 corresponding to the off position for first and second light sources 34 and 60. Multi-position switch 32 additionally includes a second position 68 corresponding to the on position of first light source 30 and a third position 70 corresponding to the on position of second light source 60. Additionally, multi-position switch 32 includes a fourth position 72 which corresponds to the on position of both first and second light sources 34 and 60. Thus, tissue contained between first and second jaws 16 and 20 may be illuminated by light from above and/or below the tissue relative to first end 34 of light pipe with fiber optic imaging bundle 36. Other controls for activating one or more light sources may be included on the handle 12 of the surgical instrument. For example, a switch may be provided for each light source and/or combination of light sources.

As shown in FIG. 3, surgical instrument 10 additionally includes a power source 74 positioned in handle 12 which is connected to multi-position switch 32 by power wires 76. It should be noted that, in this particular embodiment, power source 74 is a self-contained power source. Alternatively, power source 74 may be supplied by an external source available within an operating theater.

Referring now to FIG. 4, the use of surgical instrument 10 to view a tissue T positioned between first jaw 16 and second jaw 20 will now be described. First jaw 16 has a first tissue engaging surface 78 having a sloped distal surface 80 to facilitate movement against tissue. Second jaw 20 has a second issue engaging surface 82. During operation, the subject issue is positioned between first tissue engaging surface 78 and second issue engaging surface 82. Surgical instrument 10 is manipulated to position first jaw 16 and second jaw 20 about a tissue T which is targeted for operation. As noted above these operations may include grasping, stapling, cutting are otherwise manipulating of tissue T.

Once surgical instrument 10 has been properly positioned about tissue T, multi-position switch 32 is operated to activate one or both of first and second light sources 30 and 60. When multi-position switch 32 is moved to second position 68, first light source 30, positioned adjacent to first end 34 of light pipe with fiber optic imaging bundle 36, is activated to illuminate tissue T with a light beam 84. Light beam 84 reflects off of tissue T and into first end 34 of light pipe with fiber optic imaging bundle 36 to obtain an image of tissue T. Surgical instrument 10 is manipulated such that first and second jaws 16 and 20 move along tissue T until first and second jaws 16 and 20 are positioned adjacent the tissue TC to be operated upon and contacted by surgical instrument 10. Thereafter, surgical instrument 10 may be manipulated to perform specific operations on the target tissue TC.

Alternatively, depending upon the type of tissue T being operated on and the particular operations to be performed, multi-position switch 32 may be moved to the third position 70 activating second light source 60 so as to transmit light through target tissue TC by a light beam 86. Further, multi-position switch 32 may be moved to the fourth position 72 to illuminate of first and second light sources 30 and 60 thereby directing both reflected light beam 84 and transmitted light beam 86 relative to tissue towards first end 34 of 36 and thus obtain an image of target tissue TC at second end 38 of light pipe with fiber optic imaging bundle 36.

It should be noted that second end 38 of light pipe with fiber optic imaging bundle 36 may be constructed in various fashions to manipulate the image observed thereon. For example, second end 38 may be constructed so as to magnify the image observed to facilitate identifying the characteristics of the images being viewed. Additionally, second end 38 may be provided with various types of filters to manipulate and quantify or qualify the images transmitted therethrough.

Referring back to FIG. 2, once an image of target tissue TC has been obtained at second end 38 of light pipe with fiber optic imaging bundle 36, the image may be compared to the reference images provided by tissue comparison chart 40. For example, surgical instrument 10 can be manipulated such that the image observed at second end 38 appears similar to reference image 42 corresponding healthy tissue. Surgical instrument 10 can then be manipulated along tissue T until the image observed by second end 38 corresponds to one or more intermediate reference images 48, 50, 52 or 54. Depending upon the desired use of surgical instrument 10, surgical instrument 10 can be manipulated until the image appearing in second end 38 appears similar to reference image 44 corresponding to fully unhealthy tissue.

In this manner, surgical instrument 10 having TVC can be utilized to obtain images of tissue being operated on and comparing the images of the tissue to known reference images thereby facilitating use and positioning of surgical instrument 10 relative to target tissue to be operated upon.

Referring now to FIG. 5, there is disclosed an alternative embodiment of a surgical instrument having a TVC or surgical instrument 90 for use in manipulating and observing tissue. Surgical instrument 90 includes a handle 92 having an elongate member 94 extending distally from handle 92. A first jaw 96 is positioned on a distal end 98 of elongate member 94 and may be integrally formed therewith. A second jaw 100 is mounted for parallel movement relative to first jaw 96. Second jaw 100 includes a longitudinal portion 102 and a perpendicular portion 104 depending from a proximal end 106 of longitudinal portion 102.

Surgical instrument 90 additionally includes an actuator 108 for moving first jaw 96 and second jaw 100 parallel relative to each other. As noted hereinabove, various surgical instruments are well-known in the art for moving a pair of jaws parallel relative to each other. A particularly suitable mechanism for moving a pair of jaws parallel to each other is disclosed in U.S. Pat. No. 5,336,232 to Green at al., the entire disclosure of which is incorporated by reference herein.

Surgical instrument 90 includes a rotator 110 for rotating a nose cone portion 112 of handle 92 and elongate member 94 relative to handle 92 to properly positioned first and second jaws 96 and 102 relative to tissue.

A first light source 114 is positioned on first jaw 96 and is operated by a multi-position switch 118 provided on handle 92. A first end 118 of a light pipe with fiber optic imaging bundle 120 (FIG. 6) is provided on first jaw 96 and a second end 122 of light pipe with fiber optic imaging bundle 120 is positioned on handle 92 in a manner similar to that described hereinabove with regard to surgical instrument 10. A tissue comparison chart 124 is also provided on handle 92. Similar to that of tissue comparison chart 40 described hereinabove, tissue comparison chart 124 includes a plurality of reference images 126 which can be compared with the image observed at second end 118 of light pipe with fiber optic imaging bundle 120.

Figures 6, 7:
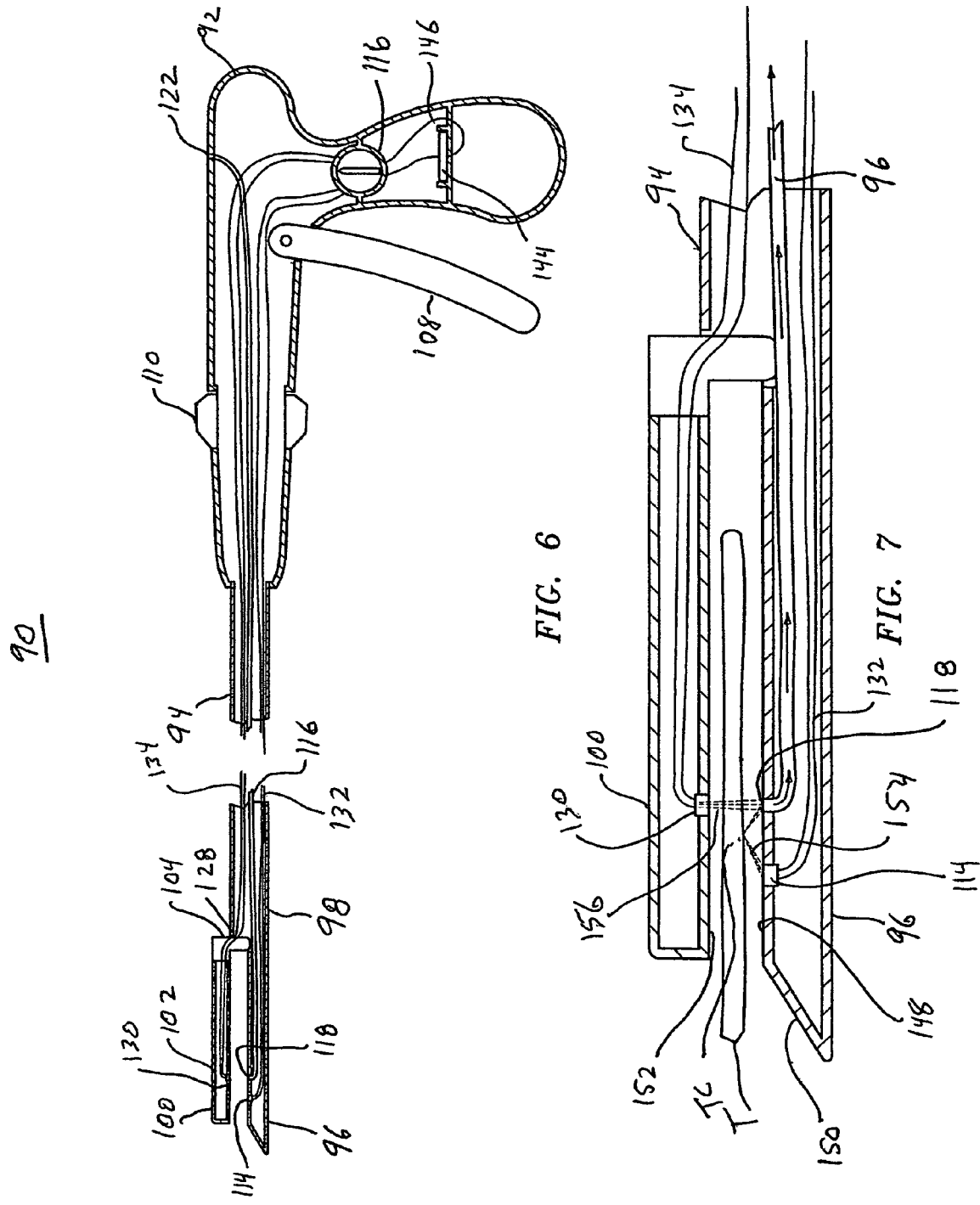
FIG. 6 is a side view, shown in section, of the surgical instrument of FIG. 5.
FIG. 7 is an enlarged side view, shown in section, of the distal end of the surgical instrument of FIG. 5.

Referring now to FIG. 6, and as noted hereinabove, first jaw 96 and second jaw 100 are movable parallel relative to each other. Distal end 98 of elongate member 94 is provided with a cut out 128 to accommodate movement of perpendicular portion 104 of second jaw 100. A second light source 130 is provided on second jaw 100 to transmit light through tissue. A first pair of wires 132 to connect first light source 118 to multi-position switch 116 and a second pair of wires 134 connects second light source 130 to multi-position switch 116.

Referring back for the moment to FIG. 5, multi-position switch 116 includes a first position 136 which corresponds to the off position of first and second light sources 114 and 130. A second position 138 corresponds to the on condition of first light source 114 and a third position 140 corresponds to the on condition of second light source 130. A fourth position 142 corresponds to the on condition of both first and second light sources 114 and 130.

With reference to FIG. 6, a power source 144 is provided within handle 92 to power first and second light sources 114 and 130. Power wires 146 connect power source 114 to multi-position switch 116. Alternatively, power source 144 may be supplied by an external source available within an operating theater.

Referring now to FIG. 7, first jaw 96 includes a first tissue engaging surface 148 and a distal sloped surface 150 to facilitate positioning relative to tissue. Similarly, second jaw 100 includes a second tissue engaging surface 152.

In use, surgical instrument 90 functions in a substantially identical manner to that of surgical instrument 10 to view images of tissue captured between first jaw 96 and second jaw 100. However, in contrast to surgical instrument 10, first jaw and second jaw 96 and 100 of surgical instrument 90 move parallel relative to each other rather than through an arc as is the case with surgical instrument 10. Specifically, surgical instrument 90 is manipulated to position first jaw 96 and second jaw 100 about a tissue T. Multi-position switch 116 is operated to turn on first light source 114 so as to project a beam of light 154 against tissue T An image of tissue T is observed through first end 118 of light pipe with fiber optic imaging bundle 116 and transmitted to second end 122 for comparison relative to reference images 126 of tissue comparison chart 124 (FIG. 5). Once the appropriate target area of tissue TC is observed through second end 122 surgical instrument 90 may be manipulated to perform the desired operation on tissue T.

Alternatively, multi-position switch 116 may be manipulated to turn on second light source 130 to project a second a light beam 156 through tissue T towards first end 118 of light pipe with fiber optic imaging bundle 116. As with surgical instrument 10 described hereinabove, multi-position switch 116 may be manipulated to third position 142 turning on both first and second light sources 114 and 130.

In this manner, surgical instrument 90 is used to grasp tissue between first and second tissue engaging surfaces 150 and 152 by parallel relative movement of jaws 96 and 100. This parallel relative movement of jaws 96 and 100 is desirable in situations where uneven compression of tissue, which would result from pivotal jaw movement, is not desired, such as, for example, during tissue measurement techniques, as well as various stapling and cutting operations.

In further embodiments, the surgical instrument has a pair of movable jaws, in which each jaw moves pivotally or in parallel with respect to the elongate member. The surgical instrument disclosed herein may incorporate one or more light pipes and light sources, or may have a light pipe and light source incorporated in a single device. In other embodiments, the housing of the instrument is formed so as to connect to a robotic or computerized surgical system, as an alternative to a surgical instrument that is manually operated and includes a handle.

It will be understood that various modifications may be made to the embodiments disclosed herein. For example, as described hereinabove, various types of light sources may be provided for an illuminating tissue and generating images thereof. Further, while the first and second light sources as well as the position of the first end of the light pipe with fiber optic imaging bundle are illustrated as being generally centrally located within their associated jaws, the structures may be provided at alternative longitudinal, as well as perpendicular, locations on the associated jaws depending upon the particular use of the surgical instrument. Additionally, more than two light sources, as well as, more than one light pipe with fiber optic imaging bundle may be associated with the surgical instrument. Therefore, the above description should not be construed as limiting, but merely as exemplifications of particular embodiments. Those skilled in the art will envision other modifications within the scope and spirit of the claims appended hereto.

The invention claimed is:

1. A surgical instrument comprising:
   a housing;
   a first jaw and a second jaw extending from the housing;
   a first light source and a second light source disposed on the first and second jaws, respectively;
   a light pipe with fiber optic imaging bundle extending between the second jaw and the housing, wherein the light pipe with fiber optic imaging bundle has a first end positioned on the second jaw and a second end positioned on the housing such that an image illuminated by the light sources on the first and second jaws is visible at the housing; and
   a tissue comparison chart integrated into the housing adjacent the second end of the light pipe, said tissue comparison chart including a plurality of reference images for comparison to the image illuminated by the light sources, wherein
   the first and second light sources are disposed on opposing surfaces of the first and second jaws, respectively,
   the first light source is spaced apart from the first end of the light pipe and transmits a first light beam that is reflected off the section of tissue and into the light pipe
   the second light source opposes the first end of the light pipe and transmits a second light beam through a section of tissue and into the light pipe.

2. The surgical instrument as recited in claim 1, wherein the housing has an elongate member extending distally from the housing, and the first jaw and the second jaw are relatively movable to each other.

3. The surgical instrument as recited in claim 2, wherein the first jaw and the second jaw are mounted for pivotal movement relative to each other.

4. The surgical instrument as recited in claim 1, wherein the first end of the light pipe with fiber optic imaging bundle is positioned on the first jaw.

5. The surgical instrument as recited in claim 1, wherein at least one light source is an LED light source.

6. The surgical instrument as recited in claim 5, wherein the housing includes a power source for the at least one LED light source and a switch to turn the at least one LED light source on and off.

7. The surgical instrument as recited in claim 1, wherein the tissue comparison chart at least partially surrounds the second end of the light pipe with fiber optic imaging bundle.

8. The surgical instrument as recited in claim 1, wherein the housing includes a power source for the first and second light sources and a switch for controlling the first and second light sources.

9. The surgical instrument as recited in claim 1, wherein the tissue comparison chart includes a first reference image corresponding to healthy tissue and a second reference image corresponding to unhealthy tissue.

\* \* \* \* \*